US012758667B2

(12) United States Patent
Paras

(10) Patent No.: US 12,758,667 B2
(45) Date of Patent: Oct. 13, 2026

(54) DISPOSABLE ANTISEPTIC WIPE APPARATUS

(71) Applicant: Benjamin S. Paras, Tucson, AZ (US)

(72) Inventor: Benjamin S. Paras, Tucson, AZ (US)

( * ) Notice: Subject to any disclaimer, the term of this patent is extended or adjusted under 35 U.S.C. 154(b) by 917 days.

(21) Appl. No.: 17/070,770

(22) Filed: Oct. 14, 2020

(65) Prior Publication Data

US 2021/0085815 A1 Mar. 25, 2021

Related U.S. Application Data

(63) Continuation of application No. 15/957,744, filed on Apr. 19, 2018, now Pat. No. 10,881,754.

(60) Provisional application No. 62/487,324, filed on Apr. 19, 2017.

(51) Int. Cl.

| | |
|---|---|
| ***A61L 2/23*** | (2006.01) |
| ***A61L 2/186*** | (2026.01) |
| ***B65D 75/30*** | (2006.01) |
| ***B65D 75/58*** | (2006.01) |
| ***B65D 83/766*** | (2025.01) |

(52) U.S. Cl.

CPC ................. *A61L 2/23* (2013.01); *A61L 2/186* (2013.01); *B65D 75/30* (2013.01); *B65D 75/5805* (2013.01); *B65D 83/766* (2025.01); *A61L 2202/18* (2013.01)

(58) Field of Classification Search

CPC ........ A61L 2/23; A61L 2/186; A61L 2202/18; B65D 75/30; B65D 75/5805; B65D 83/0038; A61F 13/00063; A61F 15/002; A61F 13/00

See application file for complete search history.

(56) References Cited

U.S. PATENT DOCUMENTS

| | | | | |
|---|---|---|---|---|
| 2,328,795 A * | 9/1943 | Finks | ................ A61F 13/47209 | 604/377 |
| 3,057,467 A | 10/1962 | Williams | | |
| 3,062,371 A * | 11/1962 | Patience | ............... A61F 15/001 | 206/440 |
| 3,136,418 A * | 6/1964 | Stanley | .................. D05B 85/00 | 206/63.3 |

(Continued)

FOREIGN PATENT DOCUMENTS

| | | | |
|---|---|---|---|
| CN | 205525789 | 8/2016 | |
| DE | 102014010987 A1 * | 9/2015 | ......... B29C 47/0057 |

(Continued)

OTHER PUBLICATIONS

English translation of WO2017204487 (Year: 2017).*

(Continued)

*Primary Examiner* — Regina M Yoo

(74) *Attorney, Agent, or Firm* — HAYES SOLOWAY P.C.

(57) ABSTRACT

A disposable antiseptic wipe apparatus includes a bacteria-proof packaging container having an interior compartment. An antiseptic wipe is infused with an antiseptic material and positioned within the interior compartment. The antiseptic wipe has a rolled cylindrical shape. A portion of packaging container is removable from the antiseptic wipe to exposed one end of the rolled, cylindrical shape of the antiseptic wipe while an unexposed end of the rolled, cylindrical shape of the antiseptic wipe is graspable by a user through the packaging container.

16 Claims, 13 Drawing Sheets

(56) References Cited

U.S. PATENT DOCUMENTS 3,768,725 A * 10/1973 Pilaro .................... A61B 50/30 206/439
3,926,311 A * 12/1975 Laske .................... A61B 50/30 206/439
4,446,965 A * 5/1984 Montiel ............... A45D 29/007 206/229
5,135,472 A * 8/1992 Hermann .......... A61F 13/01042 602/41
5,183,060 A * 2/1993 Shito ..................... A61F 13/068 602/56
5,363,986 A 11/1994 Cook
5,448,874 A 9/1995 Lemonnier
5,454,719 A * 10/1995 Hamblen ............ A61F 13/2008 433/136
5,753,246 A 5/1998 Peters
5,765,719 A 6/1998 Upham
6,007,264 A 12/1999 Koptis
6,010,001 A * 1/2000 Osborn, III ....... A61F 13/15252 206/440
6,065,591 A 5/2000 Dill et al.
6,551,265 B1 4/2003 Miguel
7,008,600 B2 3/2006 Katsigras
7,246,720 B1 7/2007 Montoya, Jr.
7,799,968 B2 9/2010 Chen et al.
7,807,118 B2 10/2010 Green
7,921,999 B1 * 4/2011 Kimball ................. A61K 9/703 206/440
7,950,864 B2 5/2011 Bauer et al.
8,602,257 B2 12/2013 Godsell
8,777,504 B2 7/2014 Shaw et al.
8,794,443 B2 8/2014 Ueda
8,940,675 B2 1/2015 Marsh et al.
8,999,073 B2 4/2015 Rogers et al.
9,039,967 B2 5/2015 Tennican et al.
9,125,600 B2 9/2015 Steube et al.
9,153,143 B2 10/2015 Maertz
9,271,616 B2 3/2016 Yaros
9,498,614 B2 11/2016 Alpert
9,561,298 B2 2/2017 Ferlic et al.
9,615,572 B1 4/2017 Yaniv
10,300,162 B2 5/2019 Joseph
2002/0023932 A1 2/2002 Faulks et al.
2003/0106812 A1 6/2003 Wilkman
2004/0091432 A1 5/2004 Dulin
2006/0015052 A1 * 1/2006 Crisp ................ A61F 13/00063 602/41
2006/0237475 A1 10/2006 Agarwal
2006/0257331 A1 11/2006 Dulin
2009/0291110 A1 11/2009 Johnson et al.
2010/0107350 A1 5/2010 Fryer
2010/0320115 A1 12/2010 Perry
2011/0034899 A1 2/2011 Thome, Jr. et al.
2011/0062178 A1 3/2011 Godsell
2011/0143312 A1 * 6/2011 McAdams ............ A61L 15/425 433/136
2011/0150955 A1 * 6/2011 Klingman ............ A61K 9/7007 424/405
2011/0204076 A1 8/2011 Kobayashi et al.
2012/0118909 A1 5/2012 Yaros
2015/0182738 A1 7/2015 Wolfenbarger
2016/0228924 A1 8/2016 Bushaw et al.
2018/0194540 A1 7/2018 Kryscio

FOREIGN PATENT DOCUMENTS

EP 0443502 8/1991
GB 190310239 A * 6/1903
GB 2046703 A * 11/1980 ........... A61F 15/001
GB 2 369 108 5/2002
JP S-63-184050 11/1988
JP H-03-256856 11/1991
JP 2004-321386 11/2004
JP 2004-359331 12/2004
WO WO2010/055892 5/2010
WO WO-2017204487 A1 * 11/2017 ......... B65D 75/5805

OTHER PUBLICATIONS

European Search Report issued in EPO application No. 18 788 621.3, dated Dec. 16, 2020 (8 pgs).
Chinese Office Action (with English translation) issued in Appln. No. 201880026343.1, dated Sep. 30, 2021 (13 pgs).
Notice of Allowance issued in Israel Appln. No. 269944, dated Oct. 1, 2021 (3 pgs).
Indian Office Action issued in Appln. No. 201927046729, dated Feb. 2, 2022, 7 pgs.
Japanese Office Action (with English translation) issued in Appln. No. 2020-507492, dated Jan. 28, 8 pgs.
Chinese Office Action (with English translation) issued in Appln. No. 201880026343.1, dated May 8, 2021 (18 pgs).
U.S. Appl. No. 15/957,744, filed Apr. 19, 2018.

* cited by examiner

DISPOSABLE ANTISEPTIC WIPE APPARATUS

CROSS REFERENCE TO RELATED APPLICATION

This application is a continuation of U.S. patent application Ser. No. 15/957,744 filed Apr. 19, 2018, which claims benefit of U.S. Provisional Application Ser. No. 62/487,324 filed Apr. 19, 2017, titled "Disposable Antiseptic Wipe Apparatus," the entire disclosure of which is incorporated herein by reference.

FIELD OF THE DISCLOSURE

The present disclosure is generally related to antiseptic wipes and more particularly is related to a disposable antiseptic wipe apparatus.

BACKGROUND OF THE DISCLOSURE

Conventional antiseptic wipes are used in hospitals to clean an injection area on a patient's body prior to an injection with a needle. They're also used to clean a peripheral IV port in a patient's arm, or other devices proximate to a patient before connecting an IV fluid to the IV port. These antiseptic wipes are commonly made from a fabric material infused with an antiseptic material(s), such as alcohol, hydrogen peroxide, iodine, polyhexanide, or others, which are folded and packaged individually in foil-lined packets. The foil-lined packets are openable at a top edge thereof, such that a user can tear open the packaging and remove the antiseptic-infused fabric material therefrom by grasping the exposed edge of the fabric material.

FIGS. 1-3 are illustrations of antiseptic wipes 10 in accordance with the prior art. Specifically, FIG. 1 illustrates a conventional antiseptic wipe 10 showing the fabric material 12 within the packaging 14 and FIG. 2 illustrates the antiseptic wipe 10 in a state where the packaging 14 has been opened to allow contact to the antiseptic-infused fabric material 12. FIG. 3 depicts the antiseptic-infused fabric material 12 after removal from the packaging 14. Commonly, the antiseptic-infused fabric material 12 is a single sheet of material which is folded into layers prior to being placed within the packaging, which can then be unfolded after removal from the packaging 14, as shown in FIG. 3. When antiseptic wipes are used, the fabric material is removed from the packaging, optionally unfolded, and then rubbed around the injection area of the patient or the IV port within the patient to clean the selected area with the antiseptic material infused in the fabric material. The contact between the antiseptic-infused fabric material 12 and the selected area on the patient is generally successful in reducing the possibility of infection or sepsis during injection or through the IV port.

However, the use of conventional antiseptic wipes 10 is not without shortcomings. While the antiseptic material rarely causes irritation to the patient's skin, due to the infrequent use of the antiseptic wipe on the patient's skin, the antiseptic material can cause significant irritations to the fingers of the nurse, doctor, or other medical professional using the antiseptic wipe numerous times a day. In fact, it is not uncommon for a medical professional to use an antiseptic wipe 30-50 times daily. With this repeated use, the fingers and thumb of the user are continually and repeatedly exposed to the antiseptic material, which leads to their fingers and thumb becoming sore, having cracked, dry skin which bleeds, and eventually leads to a decreasing of the fingerprint ridges on their skin. The effect on the user's fingers is painful and it leads to negative aesthetic issues on the user's fingers. Some users have attempted to solve this problem by wearing disposable medical gloves (latex or otherwise) when they need to use of the antiseptic wipe, but using 30-50 gloves each day is wasteful, inefficient, and expensive. A standard disposable latex glove cost a medical facility approximately $0.06 each. Over a one-year period, a medical professional who uses 50 gloves a day will cost the medical facility approximately $750. There are also significant negative environmental consequences of using so many non-biodegradable gloves.

Thus, a heretofore unaddressed need exists in the industry to address the aforementioned deficiencies and inadequacies.

SUMMARY OF THE DISCLOSURE

Embodiments of the present disclosure provide a system and method for a disposable antiseptic wipe apparatus. Briefly described, in architecture, one embodiment of the system, among others, can be implemented as follows. A disposable antiseptic wipe apparatus includes a bacteria-proof packaging container having an interior compartment. An antiseptic wipe is infused with an antiseptic material and positioned within the interior compartment. The antiseptic wipe has a rolled cylindrical shape. A portion of packaging container is removable from the antiseptic wipe to expose one end of the rolled, cylindrical shape of the antiseptic wipe while an unexposed end of the rolled, cylindrical shape of the antiseptic wipe is graspable by a user through the packaging container.

The present disclosure can also be viewed as providing a system for dispensing disposable antiseptic wipes. Briefly described, in architecture, one embodiment of the system, among others, can be implemented as follows. The system includes a dispenser having an outer housing, a retainer positioned at an exiting end of an interior of the outer housing, and an advancement mechanism positioned on the outer housing. A plurality of disposable antiseptic wipes are successively positioned within the outer housing. Each wipe includes a bacteria-proof packaging container having an interior compartment. An antiseptic wipe is infused with an antiseptic material. The antiseptic wipe is positioned within the interior compartment and has a rolled, cylindrical shape. The advancement mechanism is controllable by a user from an exterior of the outer housing to advance the plurality of antiseptic wipes toward the exiting end of the outer housing.

The present disclosure can also be viewed as providing a method of sterilizing an area with an antiseptic wipe. In this regard, one method, among others, can be broadly summarized by the following steps: grasping an antiseptic wipe infused with an antiseptic material in a bacteria-proof packaging container, wherein the antiseptic wipe has a rolled cylindrical shape; removing a portion of the packaging container to expose one end of the rolled, cylindrical shape of the antiseptic wipe; grasping an unexposed end of the antiseptic wipe over the packaging container; and wiping the area with the exposed end of the antiseptic wipe until the area is sterilized.

The present disclosure can also be viewed as providing a method of making disposable antiseptic wipe apparatus. In this regard, one method, among others, can be broadly summarized by the following steps: folding a flat sheet of an antiseptic wipe at least once; rolling the folded sheet into a cylinder; infusing the rolled sheet with an antiseptic material; and placing the rolled sheet within a bacteria-proof packaging container having an interior compartment, wherein a portion of the packaging container is removable from the antiseptic wipe to expose one end of the rolled sheet while an unexposed end of the rolled sheet is graspable by a user through the packaging container.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION

Figure 4A:
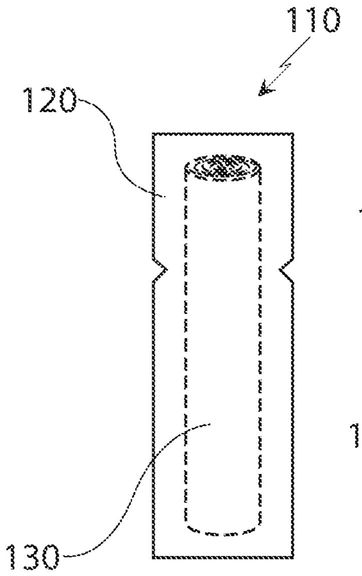
FIGS. 4A-4B are side view illustrations of a disposable antiseptic wipe apparatus, in accordance with a first exemplary embodiment of the present disclosure.
Figure 4B:
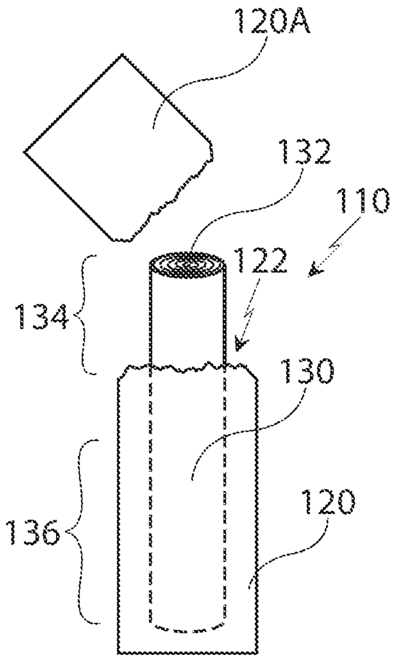
Figure 5:
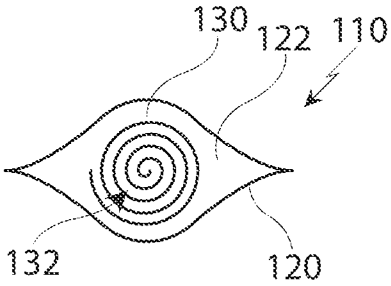
FIG. 5 is a top, cross-sectional view illustration of the disposable antiseptic wipe apparatus of FIGS. 4A-4B, in accordance with the first exemplary embodiment of the present disclosure.

FIGS. 4A-4B are side view illustrations of a disposable antiseptic wipe apparatus 110, in accordance with a first exemplary embodiment of the present disclosure. FIG. 5 is a top, cross-sectional view illustration of the disposable antiseptic wipe apparatus of FIGS. 4A-4B, in accordance with the first exemplary embodiment of the present disclosure. With reference to FIGS. 4A-5, the disposable antiseptic wipe apparatus 110, which may be referred to simply as 'apparatus 110', includes a bacteria-proof packaging container 120 having an interior compartment 122. An antiseptic wipe 130 is infused with an antiseptic material. The antiseptic wipe 130 is positioned within the interior compartment 122. The antiseptic wipe 130 has a rolled cylindrical shape 132. A portion 120A of packaging container 120 is removable from the antiseptic wipe 130 to expose one end 134 of the rolled, cylindrical shape 132 of the antiseptic wipe 130 while an unexposed end 136 of the rolled, cylindrical shape 132 of the antiseptic wipe 130 is graspable by a user through the packaging container 120.

The packaging material 120 may include a foil-based material or similar material which is bacteria-proof, water or fluid-proof and otherwise capable of preventing inadvertent contamination of the antiseptic wipe 130 while it is within the interior compartment 122 of the packaging 120. Accordingly, the packaging may be sealed along its ends and edges with known methods to maintain the interior compartment 122 in a sterile state. The antiseptic wipe 130 may be formed from a disposable fabric material or similar material which is capable of being infused or saturated with an antiseptic material. The antiseptic material may include any known antiseptic substance, including alcohol, hydrogen peroxide, iodine, polyhexanide, or others. The antiseptic wipe 130 has a rolled, cylindrical shape which may be formed by a combination of folding and rolling a flat sheet of fabric material in to a substantially tight cylinder, such that the axial rigidity of the fabric material substantially exceeds the rigidity of the fabric material in the flat sheet form. In other words, the rolled, cylindrical shape 132 allows for greatly enhanced axial deflection resistance when a lateral force is applied to one end of the antiseptic wipe 130. As shown in FIG. 5, the rolled cylindrical shape 132 may include a tight spiral with numerous overlapping layers of the fabric material, while the packaging 120 may be sized to have an interior compartment 122 which can receive the antiseptic wipe 130 in the rolled, cylindrical shape.

Prior to use of the apparatus 110, the antiseptic wipe 130 may be fully positioned within the interior compartment 122 of the packaging 120, as shown in FIG. 4A. When the apparatus 110 is needed, a user may tear off a portion 120A of the packaging 120 to expose one end 134 of the antiseptic wipe 130 in the rolled, cylindrical shape 132 while the opposing end of the antiseptic wipe 130 remains within the packaging 120, as shown in FIG. 4B. The torn portion 120A of the packaging 120 can be discarded and the antiseptic wipe 130 may be used. Use of the antiseptic wipe 130 may vary, but it may generally include two distinct types of uses. The first use is when the antiseptic wipe 130 is fully removed from the packaging 120 and applied to the patient in either the rolled, cylindrical shape 132 or after it has been unrolled and/or unfolded. This use of the antiseptic wipe 130 may be similar to how a conventional antiseptic wipe is used within the industry.

Figure 6A:
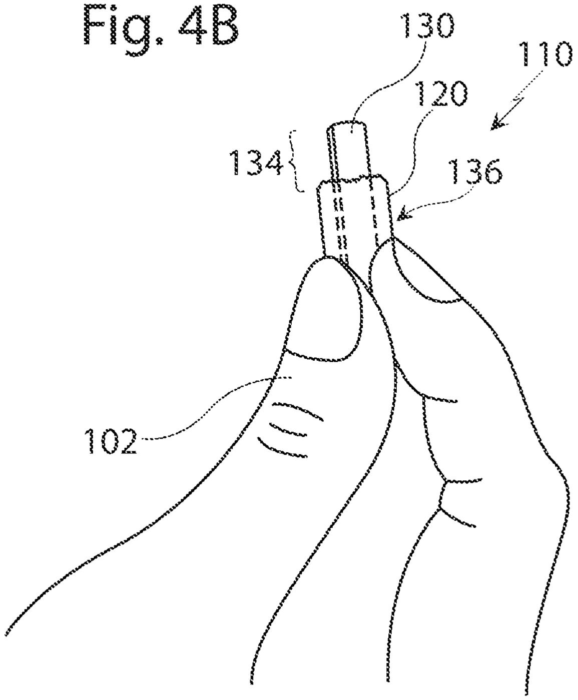
FIGS. 6A-6B are side view illustrations of the disposable antiseptic wipe apparatus being grasped by a user's fingers, in accordance with the first exemplary embodiment of the present disclosure.
Figure 6B:
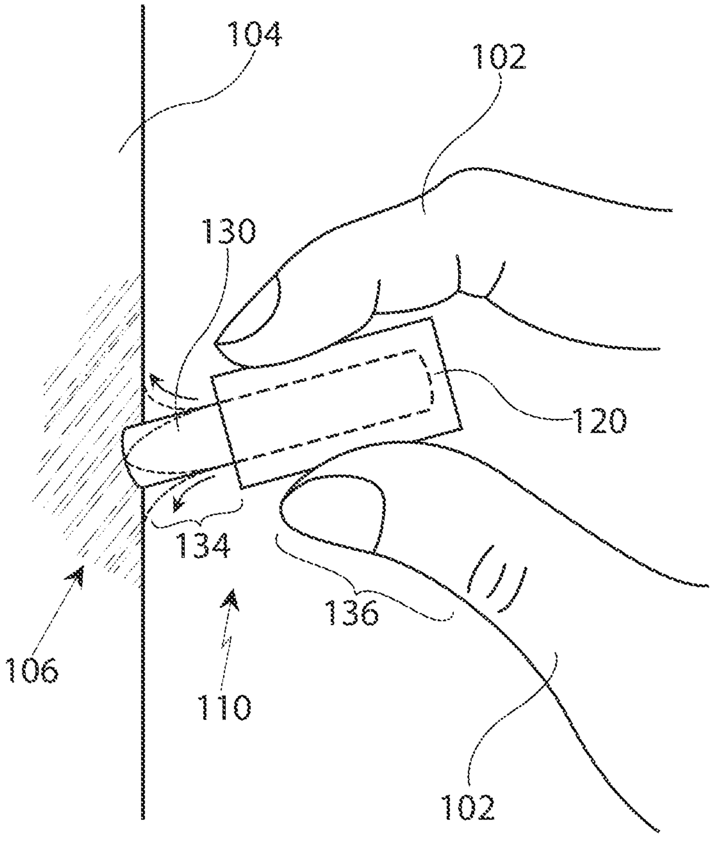

The second use of the apparatus 110 may include the antiseptic wipe 130 being used while it still remains partially housed within the packaging 120 and a user grasps the antiseptic wipe 130 through the packaging 120. FIGS. 6A-6B are side view illustrations of the apparatus 110 being grasped by a user's fingers 102, in accordance with the first exemplary embodiment of the present disclosure. As shown, the user may grasp the rolled, cylindrical antiseptic wipe 130 at the second portion 136 which remains within the packaging 120, such that the user does not need to make direct skin contact with the antiseptic wipe 130, but rather can allow the packaging 120 to act as a physical interface between the user's fingertips 102 and the antiseptic wipe 130. In this position, as shown in FIG. 6B, the user may then make contact between the exposed end 134 of the antiseptic wipe 130 and an injection area 106 on the patient 104, an IV port on the patient, or any other desired location to be cleaned, all without the user having to contact the antiseptic material infused within the antiseptic wipe 130. Since the antiseptic wipe 130 has a rolled, cylindrical shape 132, it may have sufficient durability and rigidity to be rubbed against the patient's skin along a radial direction of the antiseptic wipe 130 (e.g., using a motion similar to the motion to that of writing with a piece of chalk) or in circular motions, with sufficient force to clean the location on the patient 104 but without bending excessively, such that the antiseptic wipe 130 can apply the antiseptic material to the patient like a soft brush. The ability of the antiseptic wipe 130 to allow gentle application of the antiseptic material yet prevent axially deflecting when making contact to the patient at the exposed end 134 allows for the antiseptic wipe 130 to be used without needing disposable gloves and without the medical professional contacting the antiseptic material.

Figure 1:
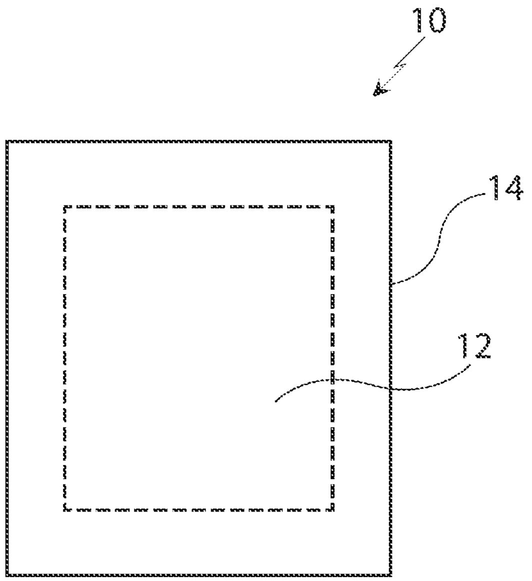
Fig. 1 Prior Art
FIGS. 1-3 are illustrations of antiseptic wipes 10 in accordance with the prior art.
Figure 2:
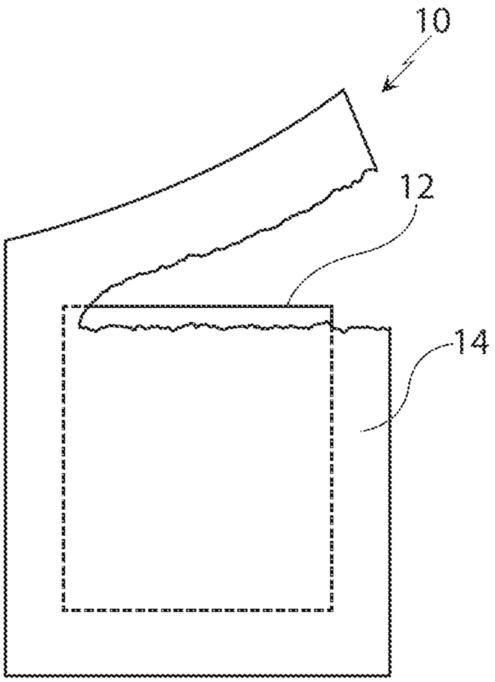
Fig. 2 Prior Art
Figure 3:
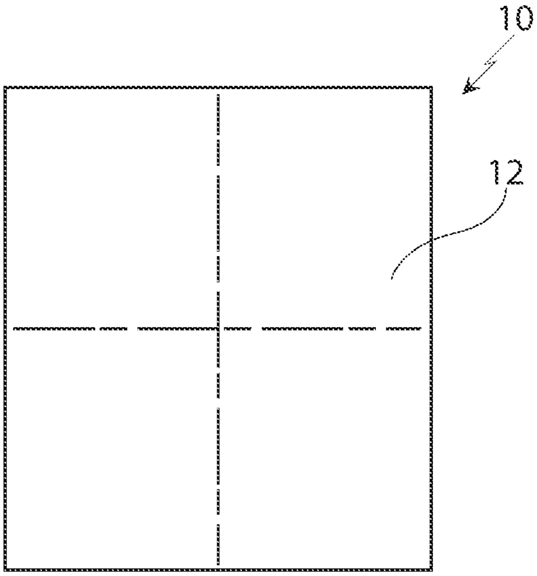
Fig. 3 Prior Art

The apparatus 110 may be used within any setting of medical field, including within medical offices, hospitals, surgical centers, or any other medical setting to clean injection areas on patients or clean medical equipment such as peripheral IV ports. Unlike conventional antiseptic wipes, which are commonly removed from their packaging and grasped by a medical professional directly with his or her fingers, the apparatus 110 may allow for the proper use of an antiseptic wipe without the user needing to contact the antiseptic material on the wipe and without the user needing to wear medical gloves. This ability is achieved, at least in part, through the use of the packaging material which partially houses the antiseptic wipe 130 and acts as a barrier between the antiseptic material within the wipe 130 and the user's fingers. The use of the rolled, cylindrical shape 132 may further enhance the apparatus' 110 use by allowing it to be effectively applied to a patient's skin while the user only grasps the packaging 120. Moreover, when a user desires using the antiseptic wipe 130 after it is fully removed from the packaging 120, being capable of doing this is no more difficult than using a conventional antiseptic wipe as described relative to FIGS. 1-3. Accordingly, the apparatus 110 is capable of improving over the deficiencies of conventional antiseptic wipes and allowing for substantially conventional use of an antiseptic wipe 130.

Figure 7A:
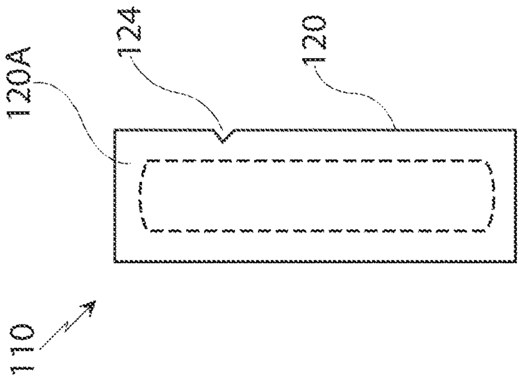
FIGS. 7A-7B are side view illustrations of the disposable antiseptic wipe apparatus with various packaging containers, in accordance with the first exemplary embodiment of the present disclosure.
Figure 7B:
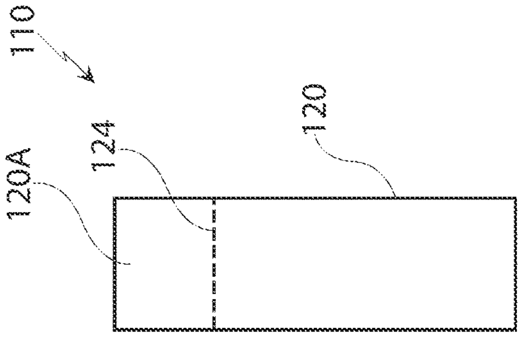

To aid in a user's ability to remove only a portion of the packaging 120 of the apparatus 110, the packaging 120 may include a tear structure 124 formed in the packaging 120. FIGS. 7A-7B are side view illustrations of the disposable antiseptic wipe apparatus 110 with various packaging containers 120, in accordance with the first exemplary embodiment of the present disclosure. As shown in FIGS. 4A-4B and 7A-7B, the tear away structures 124 may include slits, cutaways, and/or partial perforations within the packaging material 120 such that the user can easily tear away the removed portion 120A of the packaging 120. In FIG. 7A, the tear structure 124 is a cutaway positioned on one side of the packaging 120, whereas in FIG. 4A two cutaways are included. In FIG. 7B, the tear structure 124 is a partial perforation within the packaging 120. A partial perforation, e.g., where a perforation is included in an outside packaging material but not through a foil lining of the packaging 120, may be used to aid in tearing the packaging 120 while maintaining the sterile integrity of the interior compartment. A tear structure 124 may not be required in all designs, since the packaging 120 of the apparatus 110 may be capable of being torn or ripped without one. The tear structure 124 may also include markings or an indication of the location where the user should separate the removed portion 120A from the packaging 120. In one example, the tear structure 124 may be positioned axially along the packaging container 120. For instance, FIGS. 7A-7B show a tear structure 124 positioned horizontally along the packaging container 120. Vertical tear structures may be included as well. Any other types of tear structures or other structures to assist with properly opening the packaging 120 for the uses described herein may also be used, all of which are considered within the scope of the present disclosure.

Figure 8:
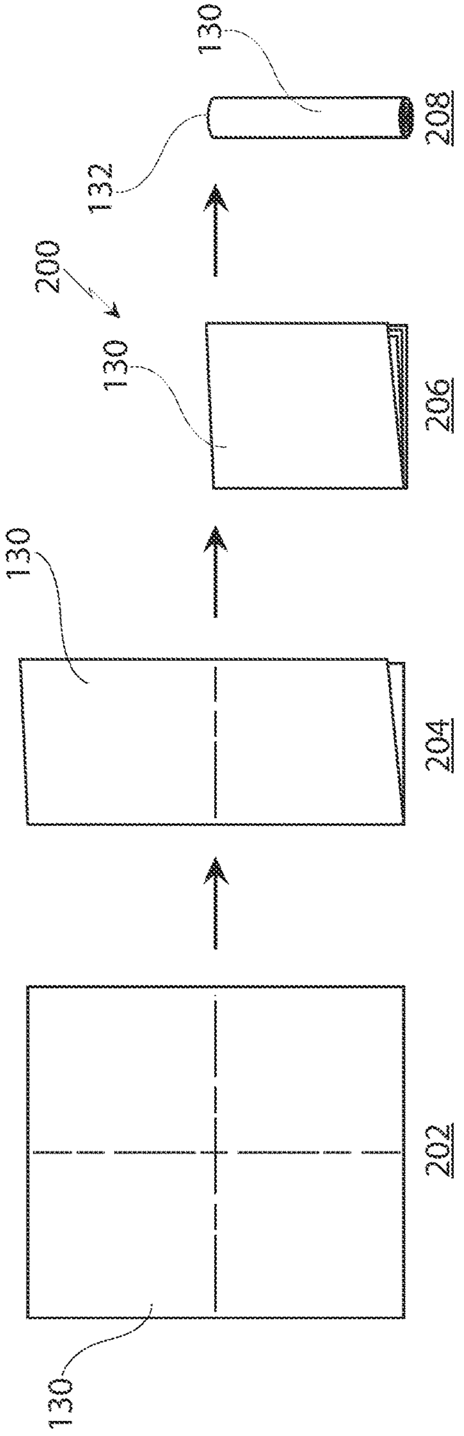
FIG. 8 is a diagrammatical flow chart of folding a disposable antiseptic wipe apparatus, in accordance with the first exemplary embodiment of the present disclosure.

FIG. 8 is a diagrammatical flow chart 200 of folding a disposable antiseptic wipe apparatus 110 of FIGS. 4A-7B, in accordance with the first exemplary embodiment of the present disclosure. In particular, FIG. 8 illustrates one example of how the antiseptic wipe 130 can be formed into the rolled, cylindrical shape 132. At block 202, the antiseptic wipe 130 may be a flat sheet of fabric material or other material, e.g., a paper or textile-based material. The antiseptic wipe 130 may be folded in half once, as shown at block 204, and then in half again as shown at block 206. As can be seen in block 206, the antiseptic wipe 130 may have four layers of material positioned proximate to each other. This folded design may then be rolled over itself into a cylinder design as shown at block 208. The rolling of the layered antiseptic wipe 130 into the cylindrical design can create axial rigidity within the resulting structure, such that it can be used as discussed relative to FIGS. 6A-6B.

FIGS. 9A-10B are isometric and side view illustrations of a disposable antiseptic wipe apparatus 910, in accordance with a second exemplary embodiment of the present disclosure.

Figure 9A:
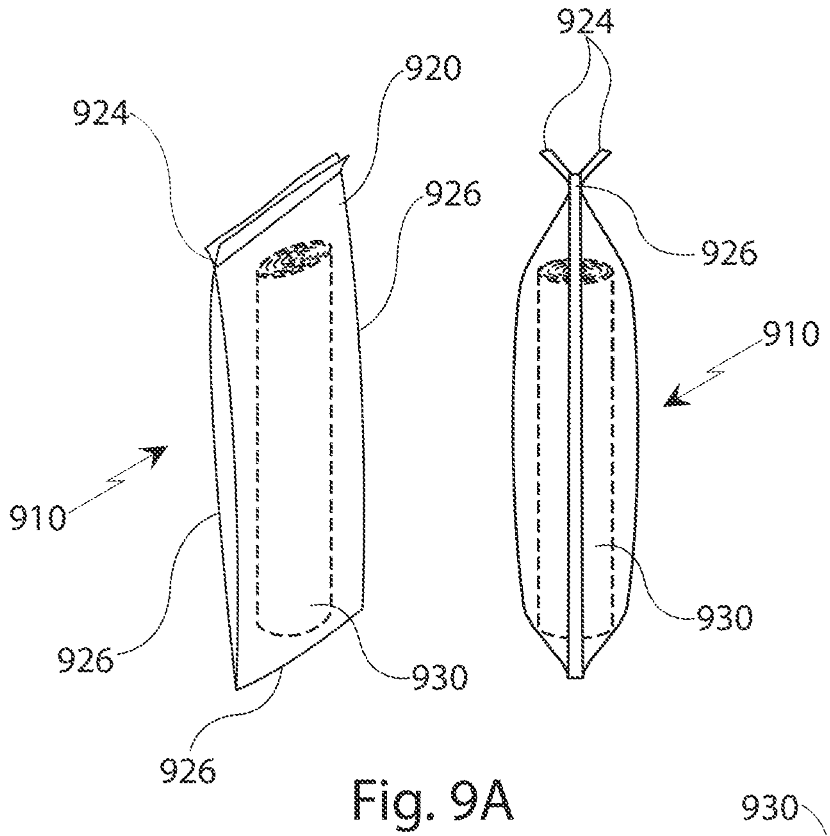
FIGS. 9A-9B are isometric and side view illustrations of a disposable antiseptic wipe apparatus, in accordance with a second exemplary embodiment of the present disclosure.
Figure 9B:
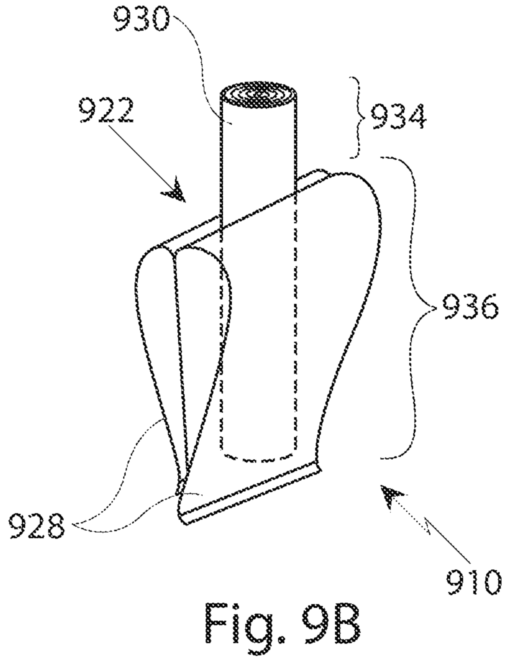

FIG. 9A shows a disposable antiseptic wipe apparatus 910 including a bacteria-proof packaging container 920 containing an antiseptic wipe 930 in a rolled, cylindrical shape. The apparatus 910 is elongate along a vertical axis of the apparatus 910. At a top end of the packaging container 920, two tabs 924 may extend away from the center of the apparatus 910. The two tabs 924 are portions of the packaging container 920 that have not been adhesively connected along an adhesive edge 926. The adhesive edge 926 may encompass the rolled antiseptic wipe 930. In one example, the adhesive edge 926 extends along the top, bottom, and sides of the apparatus 910. Any suitable adhesive may be used to adhere the packaging container 920 about the antiseptic wipe 930, including glues, epoxies, and the like. The adhesive may be light enough for a user to pull the packaging container 920 apart with little effort, but strong enough to maintain the rolled antiseptic wipe in a substantially airtight and bacteria-free environment. The tabs 924 may be used to pull apart the packaging container 920 as shown in FIG. 9B. A user may grab the tabs 924 and pull vertically along an elongate axis of the apparatus 910. This may separate one half 928 of the packaging container 920 from another half 928 along the adhesive edge 926 of the packaging container 920. When the halves 928 are separated and folded back, one end of the antiseptic wipe 930 may become an exposed end 934, while another remains an unexposed end 936. The unexposed end 936 is contained within an interior compartment 922 of the packaging container 920.

Figure 10A:
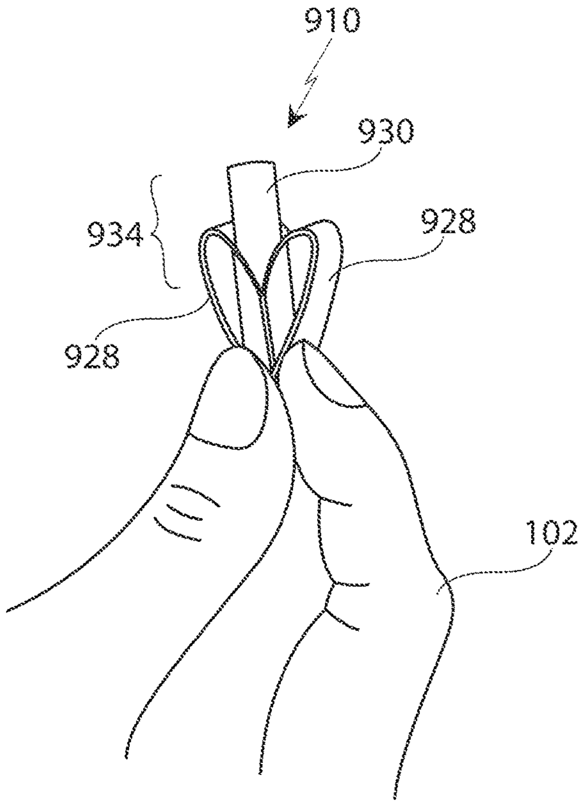
FIGS. 10A-10B are side view illustrations of the disposable antiseptic wipe apparatus being grasped by a user's fingers, in accordance with the second exemplary embodiment of the present disclosure.
Figure 10B:
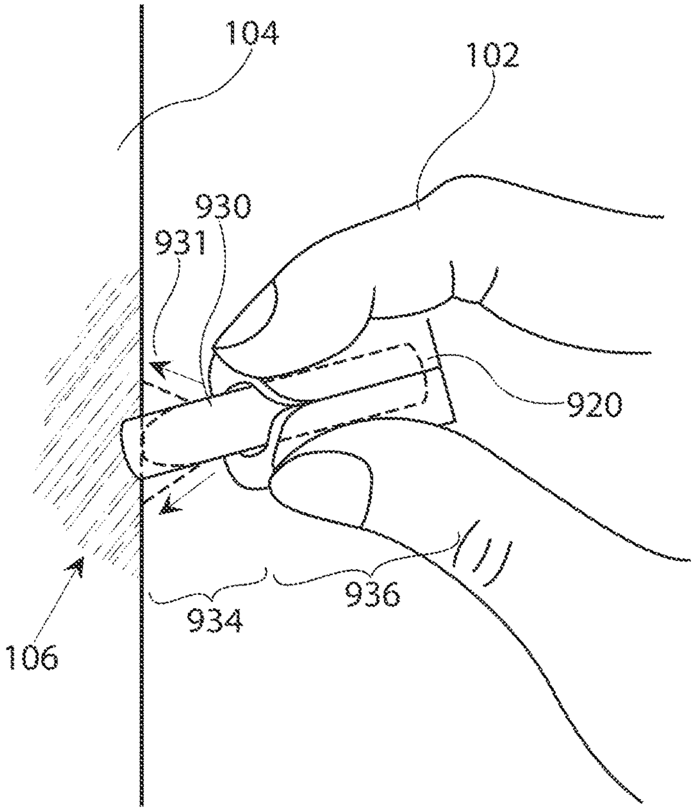

FIGS. 10A-10B are side view illustrations of the disposable antiseptic wipe apparatus 910 being grasped by a user's fingers 102, in accordance with the second exemplary embodiment of the present disclosure. After opening the packaging container 920 as discussed above, the user may fold back the halves 928 of the packaging container 920 and grasp the apparatus 910 with two or more fingers 102. The user may then apply the antiseptic wipe 930 by wiping an area, such as an injection area 106 on a patient 104. A portion 931 of the exposed end 934 of the antiseptic wipe 930 may be slightly deflected during use; however, the portion 931 may show increased axial deflection resistance due to its rolled, cylindrical shape. This increased axial deflection resistance enhances the antiseptic wipe 930's usefulness during application, as it allows the wipe 930 to be applied quickly and without unnecessary additional force to compensate for axial deflection.

FIGS. 11A-15B are illustrations of a system for dispensing disposable antiseptic wipes, in accordance with a third exemplary embodiment of the present disclosure.

In FIGS. 11A-11E, the system 1100 includes a dispenser having an outer housing 940. The outer housing 940 may be any suitable shape and size for holding and dispensing antiseptic wipes 110. In one example, the outer housing may be shaped as a hollow tube or hollow, semi-rectangular pen having an elongate vertical axis. The pen shape of the outer housing 940 may allow the antiseptic wipes 110 to be dispensed easily, one after another. The outer housing 940 may be sized to hold any suitable number of antiseptic wipes 110. The outer housing 940 may be made from any suitable rigid material, such as plastic, wood, metal, hard rubber, ceramics, and the like. The outer housing 940 should be rigid enough to provide stability for the system 110 when in use, and it may be durable enough to withstand being placed in a user's pocket. The outer housing 940 may have open ends on one or both sides of the elongate axis. The open ends may allow the antiseptic wipes 110 to travel into and out of the outer housing 940.

Figure 11A:
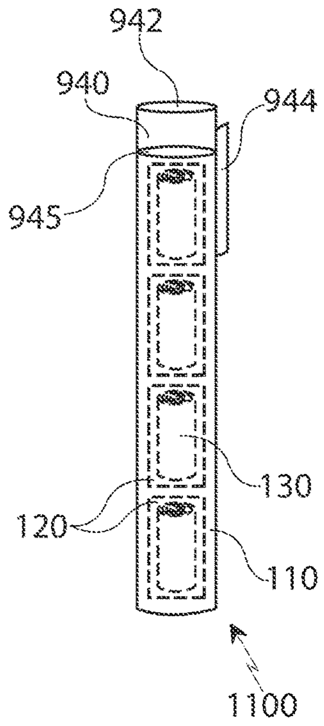
FIGS. 11A-15B are illustrations of a system for dispensing disposable antiseptic wipes, in accordance with a third exemplary embodiment of the present disclosure.
Figure 11B:
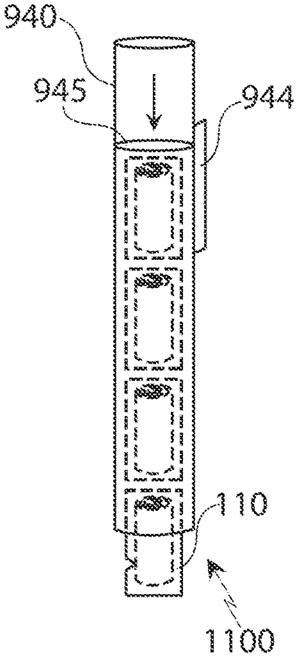
Figure 11C:
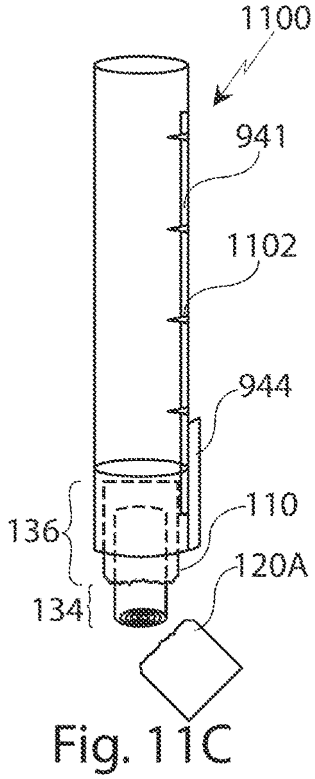

The dispenser includes an advancement mechanism 944 positioned on the outer housing 940. The advancement mechanism 944 is controllable by a user from the exterior of the outer housing 940 to advance a plurality of antiseptic wipes 110 toward the exiting end of the outer housing 940. The advancement mechanism shown in FIGS. 11A-11C is a sliding paddle 944 positioned vertically along the outside of the outer housing 940. Attached to the sliding paddle 944 is an arm 945 positioned horizontally on the interior of the outer housing 940. The sliding paddle 944 is movable along the outer housing 940 in a groove 941 located substantially along the length of the outer housing 940. The groove 941 enables the sliding paddle 944 to travel between an entrance end of the outer housing 940, shown in FIG. 11A as the top end of the outer housing, and an exiting end of the outer housing 940, shown in FIGS. 11B-11C as the end where the antiseptic wipes 110 exit the outer housing 940. When the sliding paddle 944 is moved from the entrance end to the exiting end of the outer housing 940, the arm 945 pushes the plurality of disposable antiseptic wipes 110 positioned within the outer housing 940. The antiseptic wipes 110 are successively positioned, one after another. Therefore, advancing the sliding paddle 944 along the outer housing 940 will advance each antiseptic wipe 110 through the outer housing 940.

Figure 11D:
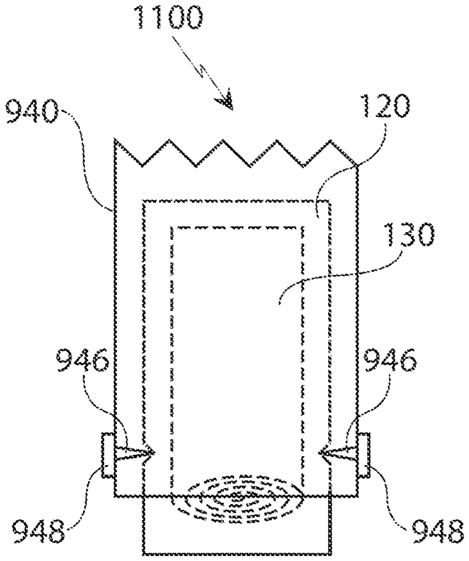

When an antiseptic wipe 110 is advanced at least partially through the outer housing as shown in FIGS. 11B-11D, a portion of the antiseptic wipe 110 is exposed for use. FIG. 11C shows that a portion 120A of the packaging container 120 may be removed from the packaging container 120 to create an exposed end 134 of the antiseptic wipe 110. The unexposed end 136 may remain wholly or partially within the outer housing 940. After use, the sliding paddle 944 may advance the used antiseptic wipe 110 completely through the outer housing 940 and advance the next antiseptic wipe 110 to be partially exposed for use. FIGS. 11A-11C show the advancement process. In FIG. 11A, the outer housing is filled with antiseptic wipes 110. In FIG. 11B, the sliding paddle 944 is used to advance an antiseptic wipe 110 for use. In FIG. 11C, the final remaining antiseptic wipe 110 is advanced and exposed for use.

In one example shown in FIG. 11C, the groove 941 includes a number of notches 1102 each spaced substantially one length of a packaging container 120 apart. The sliding paddle 944 may be shaped to catch each notch 1102 as it advances along the outer housing 940, lightly stopping the sliding paddle 944's motion. This may allow the user to advance the sliding paddle 944 from notch to notch in increments of about one packaging container 120 without needing to think about the amount of advancement needed. This may allow the system 1100 to be used quickly from sterilization site to sterilization site.

The outer housing 940 may include a removable cap 942 at an entrance end of the outer housing 940, opposite the exiting end. The removable cap 942 may prevent dust and other debris from entering the outer housing 940 through the entrance end. In one example, when the supply of antiseptic wipes 110 needs to be replaced, the cap 942 may be removed, allowing the sliding paddle 944 to be removed. The antiseptic wipes 110 may be loaded into the outer housing 940, and the sliding paddle 944 and the cap 942 replaced.

FIG. 11D shows an exemplary packaging remover 946 located on the outer housing 940. The packaging remover 946 may include a blade, edge, or other sharp object. The packaging remover 946 may be positioned on the inside of the outer housing 940 at the exiting end of the outer housing 940, and may be useful for removing a portion 120A of the packaging container 920 when the antiseptic wipe 110 is advanced partially through the outer housing 940 for use. When the desired portion of the antiseptic wipe 110 has been advanced through the outer housing 940, the user may press a button 948 located on the outer housing 940. The button 948 may be a biasing element that, when pressed, pushes the packaging remover 946 inward toward the antiseptic wipe 110. The packaging remover may cut or tear through the packaging container 120 while not touching the rolled antiseptic wipe 130 contained therein. This may cause a portion 120A of the packaging container 120 to be removed from the antiseptic wipe 110 without the user having to manually tear or otherwise remove it. In one example, the button 948 and the packaging remover 946 may be circular, and may encompass the entire circumference of the outer housing 940.

Figure 11E:
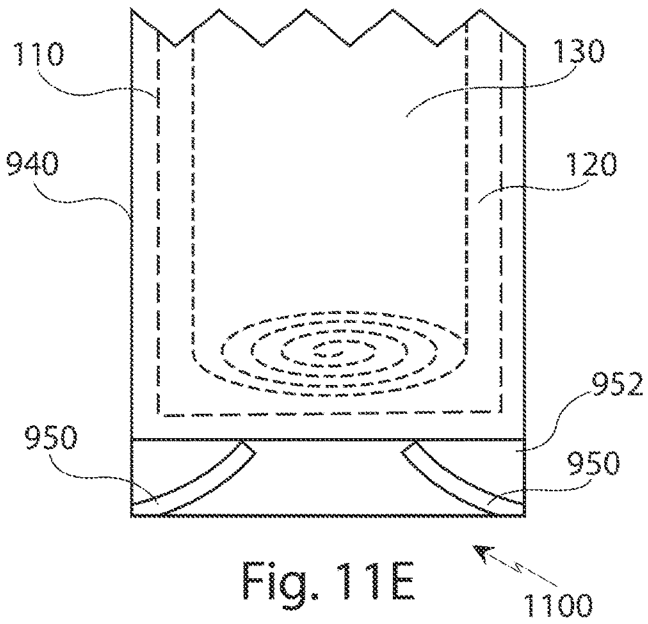

FIG. 11E shows the dispenser with a retainer 950 positioned at an exiting end of the interior of the outer housing 940. The retainer 950 may be any structure that prevents the antiseptic wipes 110 from falling out of the outer housing 940. In one example, the retainer 950 may be a flexible stopping structure extending at least partially into the path of one of the antiseptic wipes 110. The flexible stopping structure may be made of any suitable flexible material, including rubber, plastic, polymer, and the like. In the example shown in FIG. 11E, the flexible stopping structure is a rubber ring attached to the inside surface of the outer housing 940 at the bottom edge of the exiting end of the outer housing 940. The ring is curved slightly up and into the outer housing 940. The ring has an open space in the middle of the outer housing 940 to allow antiseptic wipes 110 to pass through. Initially, the open space is smaller than the diameter of the antiseptic wipe 110 so that the antiseptic wipe 110 will not move past the retainer 950 and exit the outer housing 940. When a user applies force with the advancement mechanism 944, however, the ring will flex downward, allowing enough space for the antiseptic wipe 110 to pass through. After the antiseptic wipe 110 has been used, the user may advance the used wipe out of the dispenser and continue advancing the remaining antiseptic wipes 110. The flexible stopping structure 950 may return to its initial position and prevent the next antiseptic wipe 110 from exiting the outer housing. In one example, the flexible stopping structure 950 may initially bend downward to prevent the antiseptic wipe 110 from passing through, then expand as pressure is applied by the user.

In another example, the flexible stopping structure 950 may be contained in a cap 952 that may be attached to the exiting end of the outer housing 940. The cap 952 may have a diameter and interior hole of similar size as the outer housing 940. The cap 952 may be attached by screw or pressure fit. In one example, after the system 1100 is empty of antiseptic wipes 110, a user may remove the cap 952 to refill the outer housing 940 with antiseptic wipes 110. The cap 952 may be replaced, and the system 1100 may be reused as before.

Figure 12A:
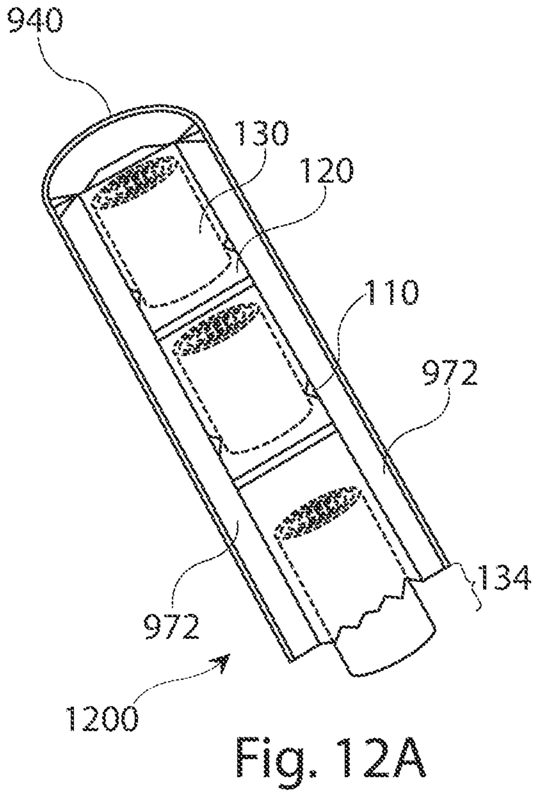
Figure 12B:
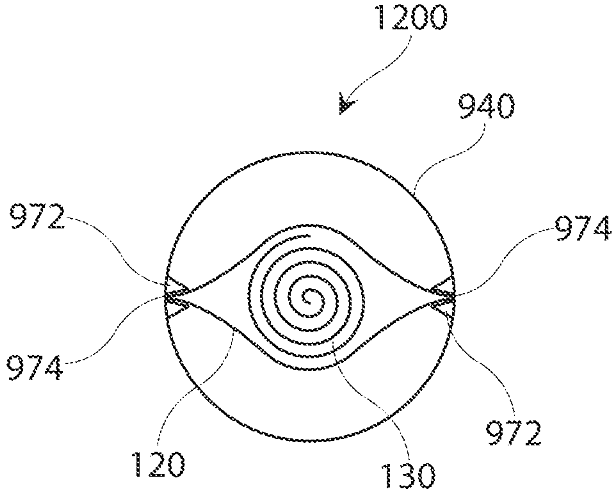

FIGS. 12A-12B show another example of a system 1200 for dispensing disposable antiseptic wipes 110. The system 1200 includes at least two tracks 972 located within the outer housing 940 and running substantially along a length of the outer housing 940. The two tracks 972 each have a groove 974. The packaging containers 120 of the plurality of antiseptic wipes 110 are alignable and movable along the grooves 974. The tracks 972 may be located substantially opposite from each other within the outer housing 940. The groove 974 down each track 972 may be sized to receive edges of the packaging container 120. The packaging containers 120 may be placed in the grooves 974 of the tracks 972 to help align the antiseptic wipes 110 as they are loaded into the outer housing 940. FIG. 12A shows a cross-sectional view of the system 1200 along the elongate axis of the outer housing. The antiseptic wipes 110 are loaded in vertically and slide down along the tracks 972. FIG. 12B shows an overhead view of the system 1200, indicating where the edges of the packaging container 120 fit into the grooves 974 of the tracks 972.

Figure 13A:
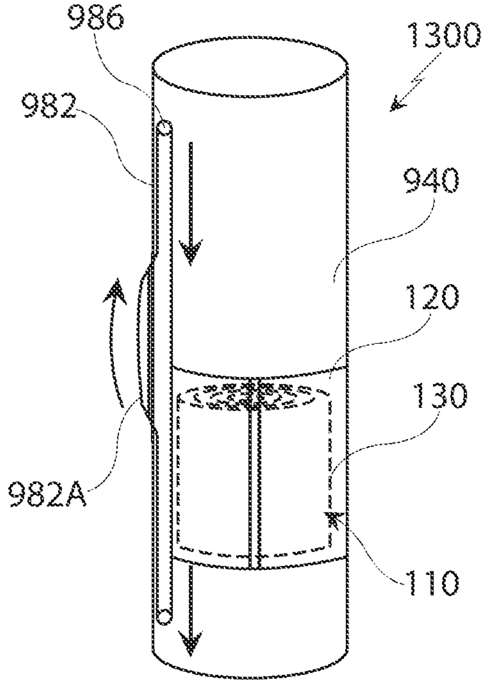
Figure 13B:
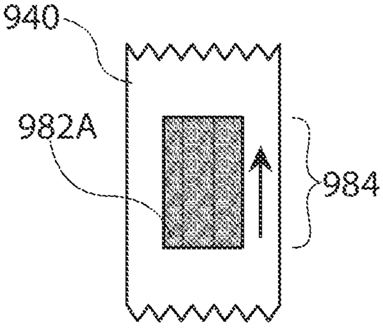

FIGS. 13A-13B show another example of a system 1300 for dispensing disposable antiseptic wipes 110. In FIG. 13A, the advancement mechanism is shown as a belt 982 located at least partially within the outer housing 940 and running substantially along a length of the outer housing 940. The belt 982 contacts the plurality of antiseptic wipes 110 inside the outer housing 940, and movement of the belt 982 causes the antiseptic wipes 110 to advance toward the exiting end of the outer housing 940. The belt 982 may be made from any suitable durable material for making belts. The belt 982 may be run around internal bearings 986 connected to the interior of the outer housing 940. The belt 982 forms a loop that runs substantially the length of the outer housing 940. The loop acts as an advancement mechanism for the antiseptic wipes 110 by forcing the antiseptic wipes 110 to move through contact. On the outside of the outer housing 940, a portion 982A of the belt 982 may be exposed and touchable by a user. FIG. 13B shows a close-up of portion 982A on the outer housing 940. The user may advance portion 982A in an upward direction 984 using their finger. The upward direction 984 becomes a downward direction on the inside of the outer housing 940, and moves the antiseptic wipes 110 toward the exiting end of the outer housing 940.

Figure 14B:
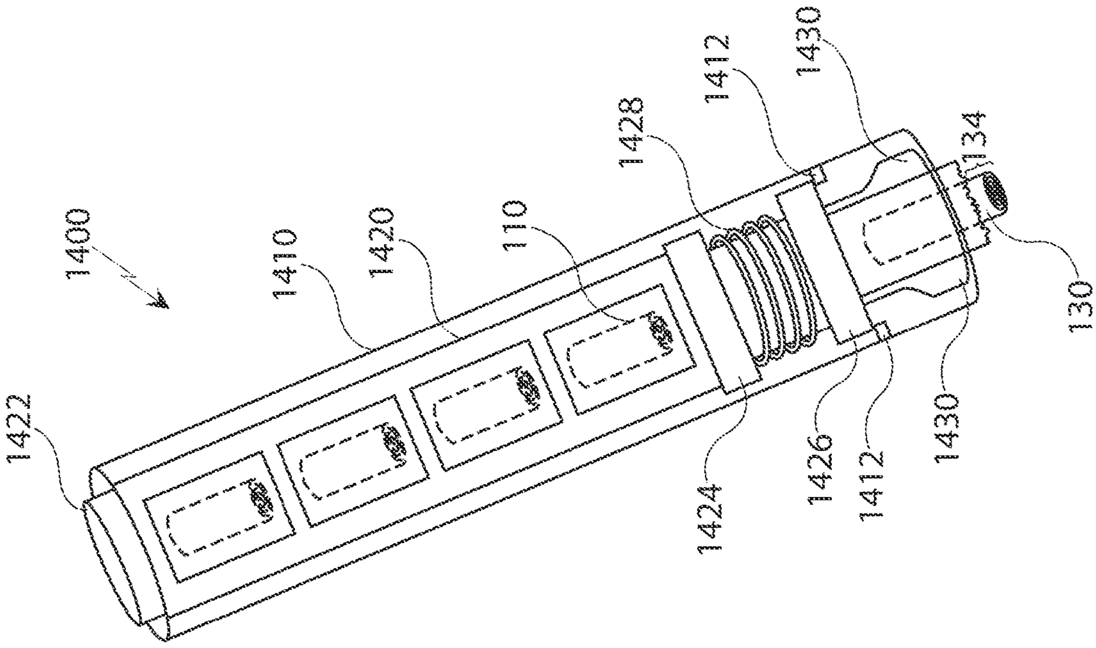
Figure 14A:
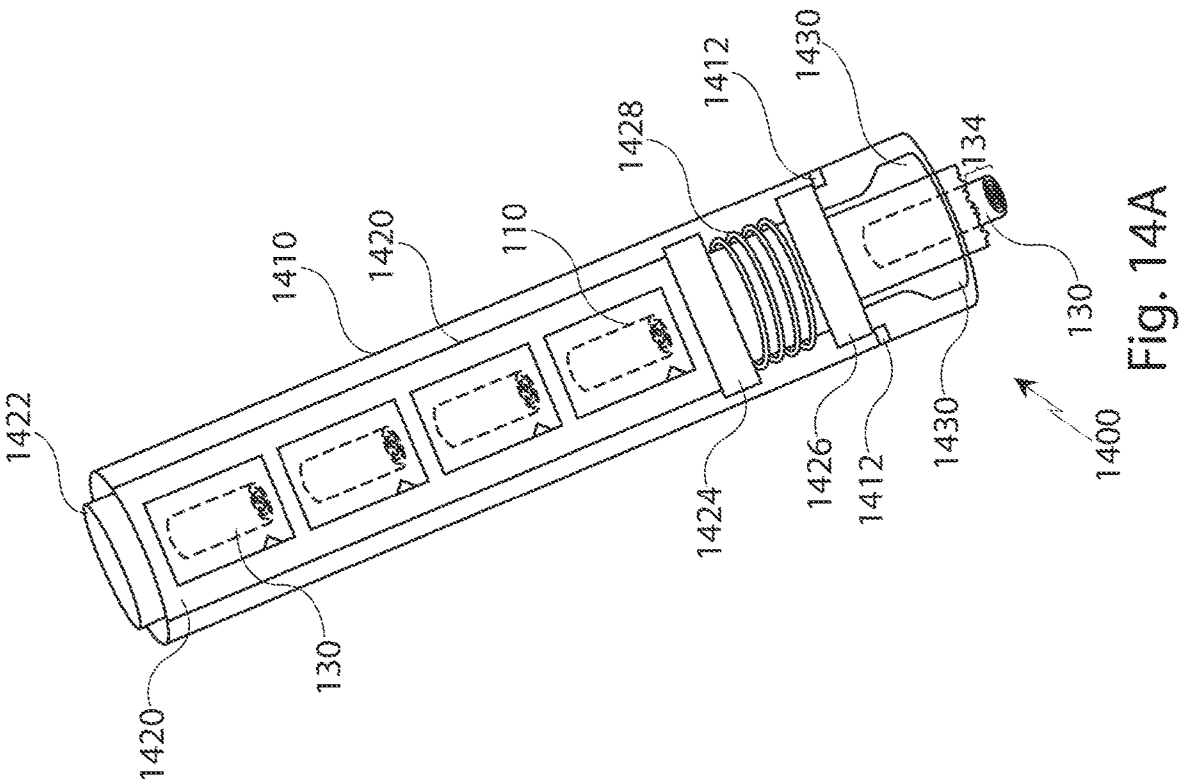

FIGS. 14A-14B show another example of a system 1400 for dispensing disposable antiseptic wipes 110. In FIG. 14A, the system 1400 has an outer housing 1410 and an inner housing 1420. The inner housing 1420 is located within the outer housing 1410. A bias able button 1422 is located on the inner housing 1420 opposite from the exiting end of the outer housing 1410. The button 1422 protrudes from the outer housing 1410 to enable a user to press the button 1422. The button 1422 and the inner housing 1420 may be made from materials similar to the outer housing 1410, including, plastic, metal, wood, rubber, ceramics, and the like. The inner housing 1420 may include a first sleeve 1424 around which a spring 1428 or other flexible element is placed. The first sleeve 1424 may provide an edge for the spring 1428 to bias against. The outer housing 1410 may include a shelf 1412 near the exiting end of the outer housing 1410. A second sleeve 1426 may be positioned around the inner housing 1420 and resting against the shelf 1412. When the button 1422 is pressed, the inner housing 1420 is moved though the outer housing 1410 toward the exiting end. The first sleeve 1424 and the second sleeve 1426 may press against the spring 1428 as the inner housing 1420 moves relative to the shelf 1412 of the outer housing 1410, compressing the spring 1428. When the button is released, the spring 1428 may bias against the first sleeve 1424, returning the inner housing 1420 to its original position.

The system 1400 includes a plurality of antiseptic wipes 110 stacked in succession within the inner housing 1420. A plurality of clutch arms 1430 are located on the inner housing 1420 at the exiting end of the outer housing 1410. The clutch arms 1430 function to advance the antiseptic wipes 110 and hold the foremost antiseptic wipe 110 in position for use.

FIG. 14B shows the clutch arms 1430 in an initial, closed, clutching position. The clutch arms 1430 are pressed against the foremost antiseptic wipe 110, holding it in position for use. The exposed portion 134 of the rolled antiseptic wipe 130 protrudes from the outer housing, allowing a user to wipe an area with the exposed portion 134. When the antiseptic wipe 110 has been used, it may be discarded by pressing the button 1422 between one and several times. During each press of the button 1422, the inner housing 1420 advances downward, pushing the plurality of antiseptic wipes 110 forward relative to the outer housing 1410. At the same time, the clutch arms 1430, which are attached to the inner housing 1420, are pushed in the same direction and allowed to expand to fill the space of the outer housing 1410, causing them to open as shown in FIG. 14A. The foremost antiseptic wipe 110 is advanced. As the button 1422 is released, the clutch arms 1430 return to their original positions, closing again on the advanced antiseptic wipe 110. After enough button presses, the foremost antiseptic wipe 110 may be removed from the system 1400 and discarded. The next antiseptic wipe 110 is advanced to a position for use.

Figure 15A:
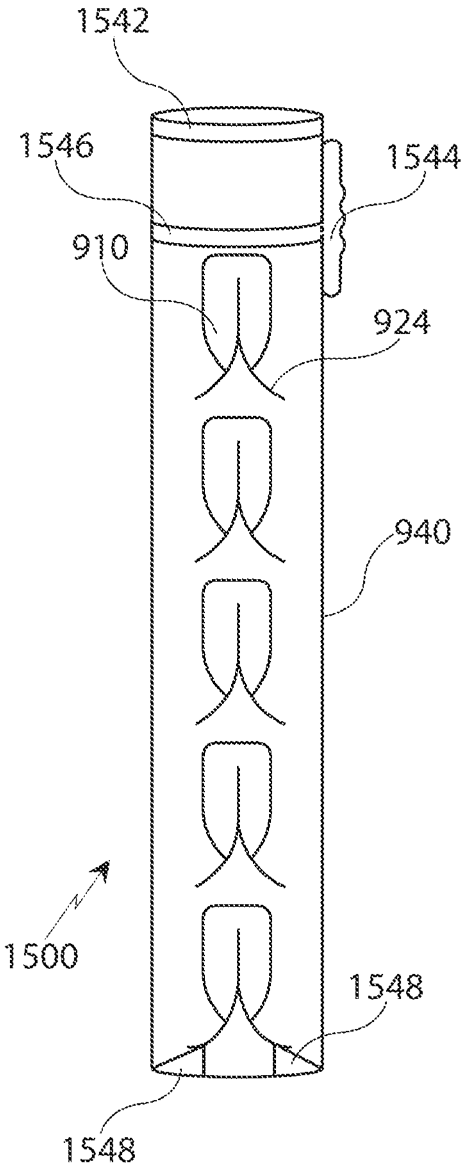
Figure 15B:
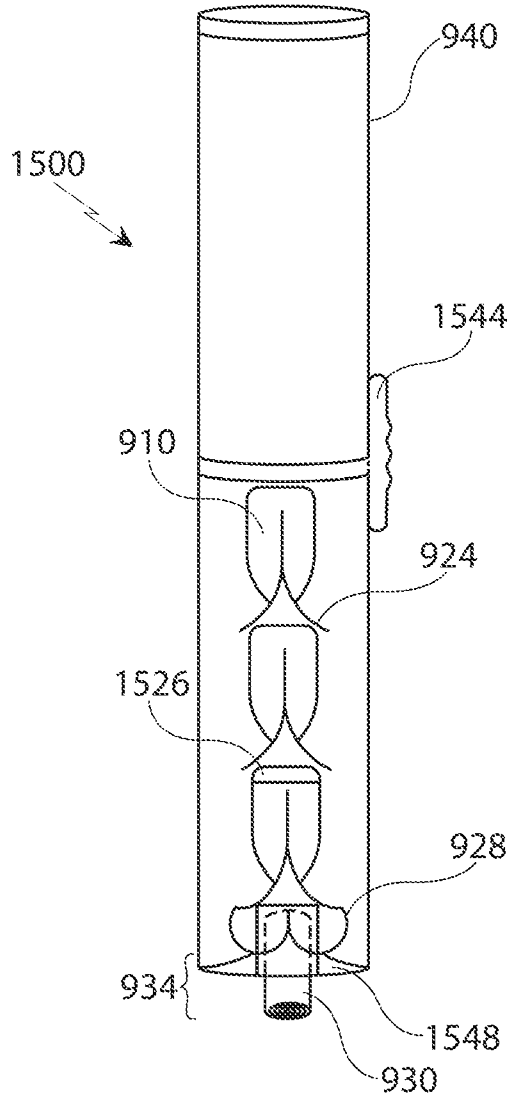

FIGS. 15A-15B show a system 1500 with the sliding paddle 1544 advancement mechanism using the antiseptic wipe apparatus 910 of FIGS. 9A-10B ("antiseptic wipes 910"). FIG. 15A shows the system 1500 having an outer housing 940, a sliding paddle 1544 and arm 1546, and a plurality of antiseptic wipes 910. In one example, the outer housing 940 may include a top or cap 1542 that may be removed to allow the system 1500 to be reloaded.

The system 1500 may include a structure to de-sheath the packaging container 930 from the rolled antiseptic wipe 920 of each of the antiseptic wipes 910. The structure may be a sharp edge 1548 located at the exiting end of the outer housing 940. In one example, the edge 1548 may be a ring located on the interior of the outer housing 940. The ring may leave an open space large enough for the antiseptic wipes 910 to pass through as they are advanced through the system 1500. The sharp edge 1548 may be sized and positioned to catch the tabs 924 of the antiseptic wipes 910 as they are pushed through the outer housing 940. As shown in FIG. 15B, this may cause the tabs to pull open at the sharp edge 1548, separating the packaging container 920 into halves 928 along the adhesive edges. The exposed portion 934 of the rolled antiseptic wipes 930 may be ready for use in sterilization. This may allow the system 1500 to self-open the antiseptic wipes 910 as they are advanced into position for use. In one example, the antiseptic wipes 910 include a base where the packaging container 920 will not separate from the rolled antiseptic wipes 930. This may allow a user to dispose of a used antiseptic wipe 910 without touching the wipe. Instead, the user may advance the sliding paddle 1544 to dispose of the used antiseptic wipe 910.

Figure 16A:
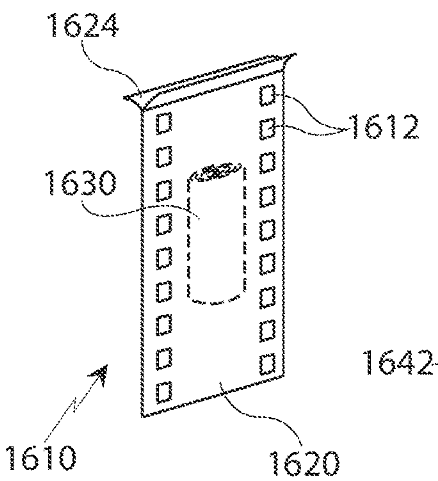
FIGS. 16A-16C are illustrations of an apparatus and system for dispensing disposable antiseptic wipes, in accordance with a fourth exemplary embodiment of the present disclosure.
Figure 16B:
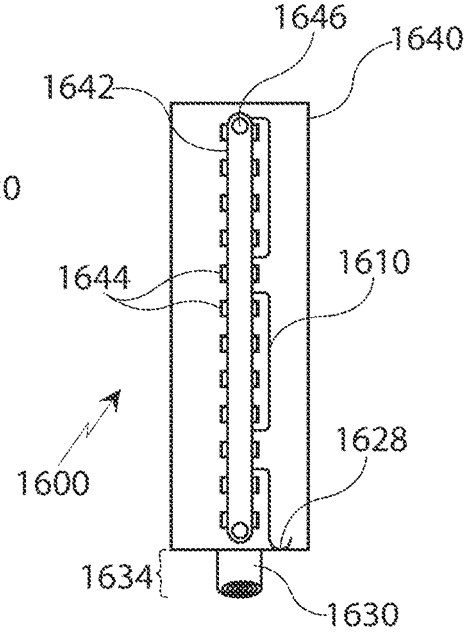
Figure 16C:
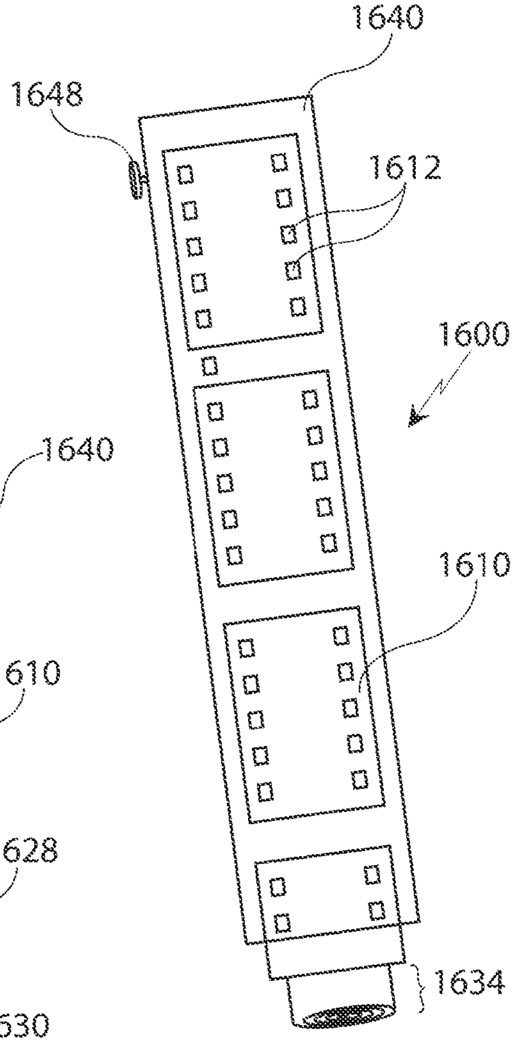

FIGS. 16A-16C are illustrations of an apparatus and system for dispensing disposable antiseptic wipes, in accordance with a fourth exemplary embodiment of the present disclosure.

FIG. 16A shows a disposable antiseptic wipe apparatus 1610 including a packaging container 1620 and rolled, cylindrical antiseptic wipe 1630 as disclosed above. Additionally, the apparatus 1610 includes a plurality of perforations 1612 along two opposite sides of the packaging container 1620. The perforations 1612 may be included along substantially the entirety of the packaging container 1620, and may be used to guide the apparatus 1610 when used in a system 1600 for dispensing disposable antiseptic wipes.

FIGS. 16B-16C show the system 1600. The system 1600 includes an outer housing 1640 and a plurality of antiseptic wipes 1610 within the outer housing 1640. The system 1600 also includes a gear belt 1642 located within the outer housing 1640 and running substantially the length of the outer housing 1640. The gear belt 1642 has teeth 1644 all along the gear belt 1642 that advance as the gear belt 1642 is advanced. The gear belt 1642 may be wound around internal bearings 1646 or other structures within the outer housing 1640. The antiseptic wipes 1610 may be aligned with the teeth 1644 through the perforations 1612. The antiseptic wipes 1610 may be fed into the outer housing 1640, where the teeth 1644 may engage with the perforations 1612 to align and advance the antiseptic wipes 1610. FIG. 16C shows the antiseptic wipes 1610 aligned with the teeth 1644 and in successive positions within the outer housing 1640. A wheel 1648 may be located on the exterior of the outer housing 1640 and may be in mechanical connection with the bearings in FIG. 16B. A user may turn the wheel 1648 to engage the gear belt 1642, which may in turn advance the antiseptic wipes 1610 toward the exiting end of the outer housing 1640. Once the gear belt 1642 has been sufficiently advanced to expose one of the antiseptic wipes 1610, the packaging container 1630 may be automatically or manually removed as described above, and the exposed portion 1634 may be used to sterilize an area.

Figure 17:
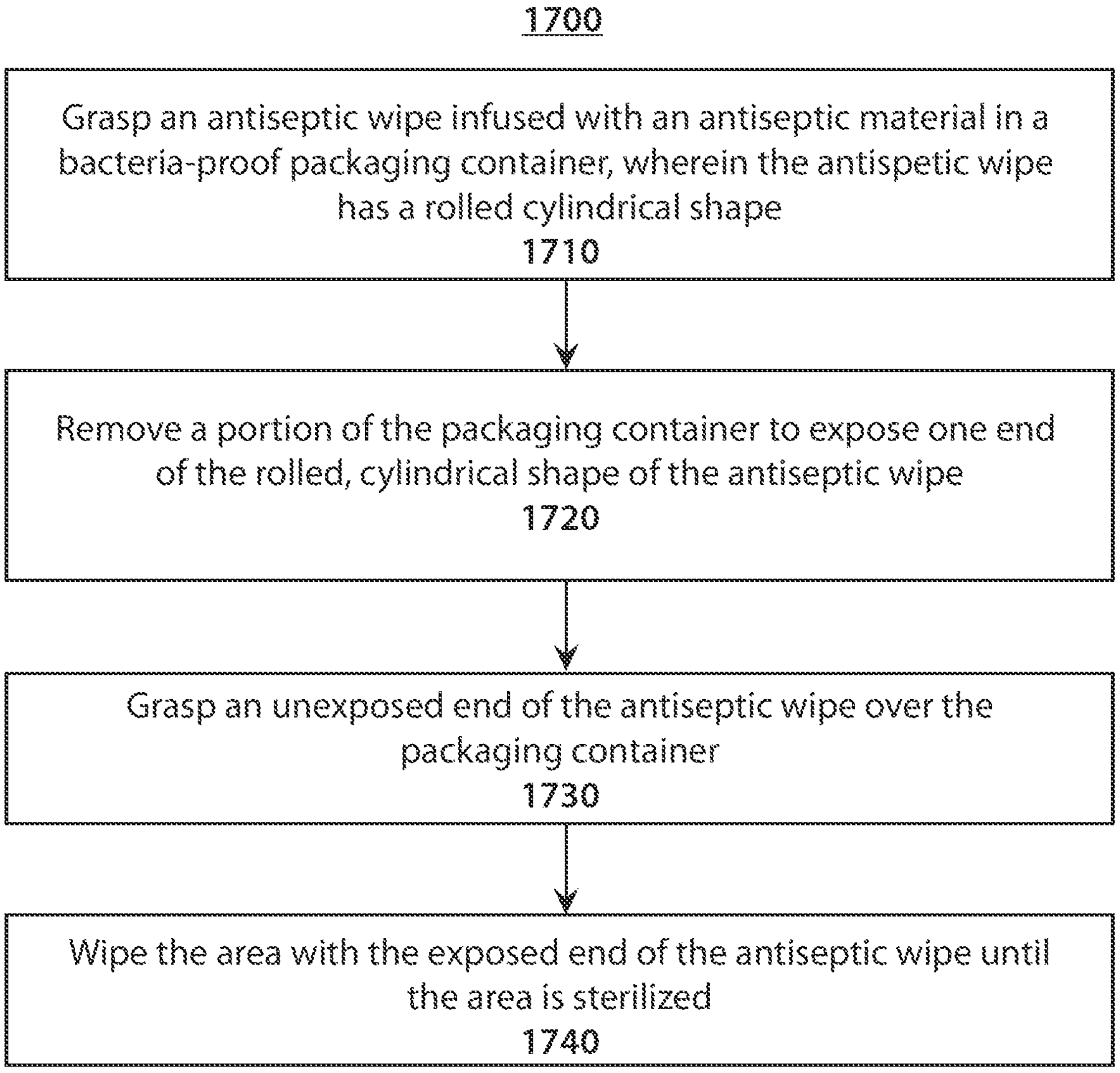
FIG. 17 is a flow chart illustrating a method of sterilizing an area with an antiseptic wipe.

FIG. 17 is a flow chart illustrating a method 1700 of sterilizing an area with an antiseptic wipe. It should be noted that any process descriptions or blocks in flow charts should be understood as representing modules, segments, or steps that include one or more instructions for implementing specific logical functions in the process, and alternate implementations are included within the scope of the present disclosure in which functions may be executed out of order from that shown or discussed, including substantially concurrently or in reverse order, depending on the functionality involved, as would be understood by those reasonably skilled in the art of the present disclosure.

Step 1710 includes grasping an antiseptic wipe infused with an antiseptic material in a bacteria-proof packaging container, wherein the antiseptic wipe has a rolled cylindrical shape.

Step 1720 includes removing a portion of the packaging container to expose one end of the rolled, cylindrical shape of the antiseptic wipe. The packaging container may be torn, pulled apart, peeled, or otherwise separated from the rolled antiseptic wipe. In one example, the removed portion of the packaging container may be less than half of the packaging container. This may allow a user to apply a strong grip while using the antiseptic wipe.

Step 1730 includes grasping an unexposed end of the antiseptic wipe over the packaging container. The unexposed end may still be covered by a portion of the packaging container; therefore, the antiseptic material may not be in contact with the exterior of the unexposed end. A user may grasp the unexposed end without touching any of the antiseptic material or the rolled wipe directly. At this point, the partially exposed, rolled wipe and the unexposed portion of the rolled wipe in the packaging container provide a sturdy, non-abrasive wiping apparatus for users. The rolled shape of the wipe provides increased axial deflection in use, meaning that the antiseptic wipe can be used with usual force while sterilizing. And the protective cover of the packaging container provides insulation for users who must repeatedly use such wipes over long timelines.

Step 1740 includes wiping the area with the exposed end of the antiseptic wipe until the area is sterilized.

Figure 18:
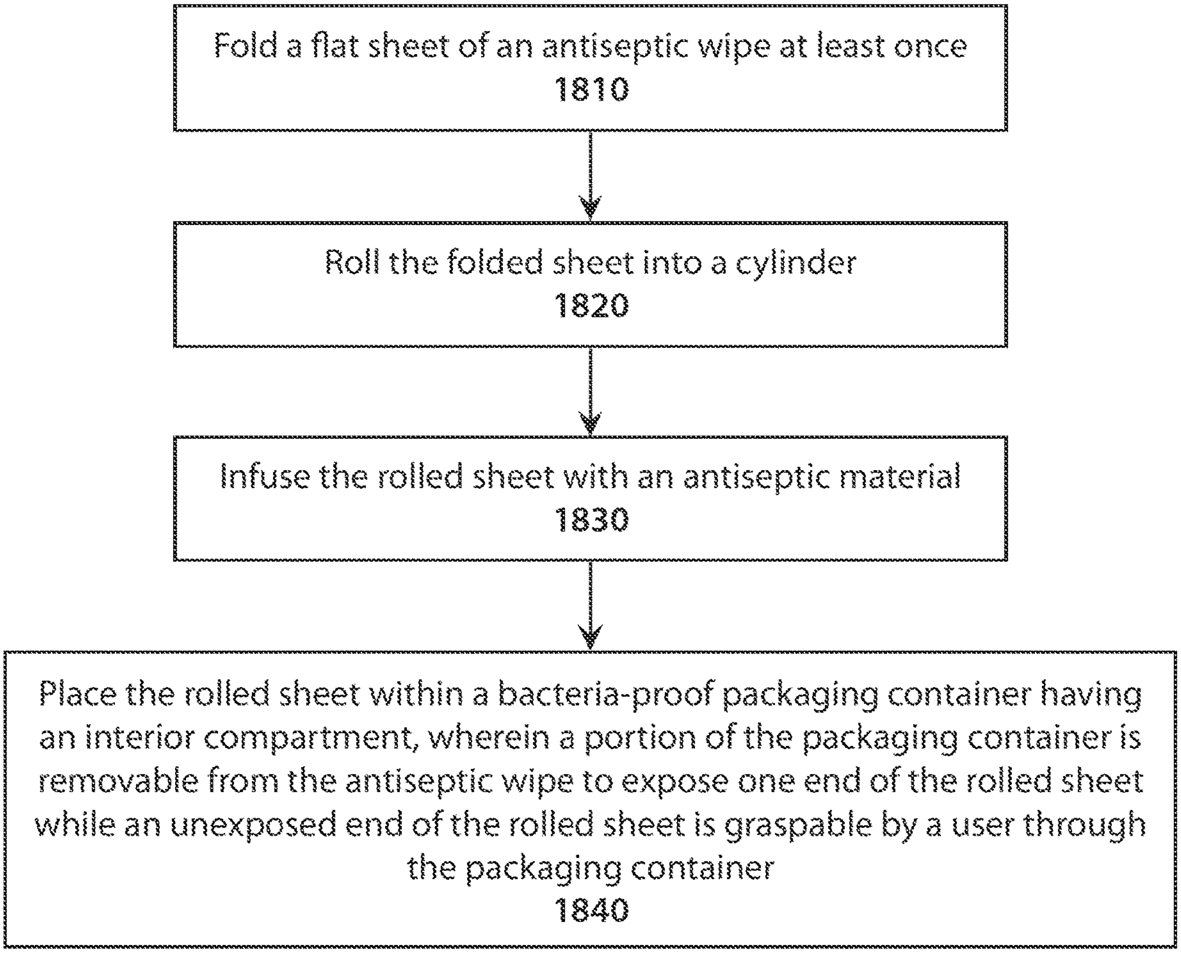
FIG. 18 is a flow chart illustrating a method of making a disposable antiseptic wipe apparatus.

FIG. 18 is a flow chart illustrating a method 1800 of making a disposable antiseptic wipe apparatus.

Step 1810 includes folding a flat sheet of an antiseptic wipe at least once. In one example, the flat sheet may be folded a plurality of times in order to achieve a desired size, shape, or layer thickness. This may depend on the initial size of the flat sheet and the desired size of the completed antiseptic wipe apparatus.

Step 1820 includes rolling the folded sheet into a cylinder. In one example, the cylinder has an elongate shape such that the length between the ends of the cylinder is more than the diameter of the cylinder. An elongate shape may be useful for grasping without touching the antiseptic materials when the antiseptic wipe is used later.

Step 1830 includes infusing the rolled sheet with an antiseptic material. This may be done by methods commonly used for infusing sheets with antiseptic materials.

Step 1840 includes placing the rolled sheet within a bacteria-proof packaging container having an interior compartment, wherein a portion of the packaging container is removable from the antiseptic wipe to expose one end of the rolled sheet while an unexposed end of the rolled sheet is graspable by a user through the packaging container. The rolled sheet may be placed on one half of a packaging container. Adhesive may be applied along the edges of the half of the packaging container, and a second half may be applied to the first half. The halves may bond together, sealing the antiseptic wipe for later use.

It should be emphasized that the above-described embodiments of the present disclosure, particularly, any "preferred" embodiments, are merely possible examples of implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure and the present disclosure and protected by the following claim.

What is claimed is:

1. A disposable antiseptic wipe apparatus for cleaning a patient's skin before a medical procedure, the disposable antiseptic wipe apparatus comprising:

a bacteria-proof packaging container having an interior compartment, the bacteria-proof packaging container being non-resealable after opening;

an antiseptic wipe infused with an antiseptic material, the antiseptic wipe being positioned within the interior compartment of the bacteria-proof packaging container without additional antiseptic wipes, and wherein the antiseptic wipe has a rolled cylindrical shape formed as a tight spiral with multiple overlapping layers; and a first portion of the bacteria-proof packaging container tearable from a second portion of the bacteria-proof packaging container, wherein the first portion is separatable from the second portion to expose one cylindrical end of the antiseptic wipe in the rolled cylindrical shape while another cylindrical end of the antiseptic wipe in the rolled cylindrical shape remains within the bacteria-proof packaging container, wherein a user only touches the bacteria-proof packaging container when contacting the exposed cylindrical end of the antiseptic wipe in the rolled cylindrical shape to the patient's skin, and wherein the rolled cylindrical shape of the antiseptic wipe has an axial rigidity that substantially exceeds the rigidity of fabric material of the antiseptic wipe in a flat sheet form to resist axial deflection of the antiseptic wipe when the exposed cylindrical end of the antiseptic wipe is contacted against the patient's skin and a lateral force is applied to the exposed cylindrical end of the antiseptic wipe.

2. The disposable antiseptic wipe apparatus of claim 1, wherein the bacteria-proof packaging container further comprises a horizontal tear structure positioned substantially proximate to the first portion of the bacteria-proof packaging container.

3. The disposable antiseptic wipe apparatus of claim 1, wherein the bacteria-proof packaging container further comprises a vertical tear structure positioned between the first portion and the second portion, and axially along the bacteria-proof packaging container.

4. The disposable antiseptic wipe apparatus of claim 1, wherein the bacteria-proof packaging container further comprises a vertical tear structure positioned between the first portion and the second portion, and axially along the bacteria-proof packaging container, wherein the vertical tear structure is connected to at least one tab pullable by the user to open the bacteria-proof packaging container along an elongate axis, and wherein the first portion of the bacteria-proof packaging container separates from the second portion of the bacteria-proof packaging container along an adhesive edge.

5. The disposable antiseptic wipe apparatus of claim 1, wherein the bacteria-proof packaging container further comprises a plurality of perforations along two opposite sides of the bacteria-proof packaging container, and wherein the disposable antiseptic wipe apparatus is guidable along a belt by the plurality of perforations.

6. The disposable antiseptic wipe apparatus of claim 1, wherein the first portion of the bacteria-proof packaging container is smaller than the second portion of the bacteria-proof packaging container in which the antiseptic wipe in the rolled cylindrical shape remains.

7. The disposable antiseptic wipe apparatus of claim 1, wherein the antiseptic wipe in the rolled cylindrical shape is not folded.

8. The disposable antiseptic wipe apparatus of claim 1, wherein the antiseptic wipe in the rolled cylindrical shape is also folded.

9. A single-use, disposable antiseptic wipe apparatus for use by a medical professional to clean a patient's skin before a medical procedure, the single-use, disposable antiseptic wipe apparatus comprising:

a bacteria-proof packaging container having an interior compartment, the bacteria-proof packaging container being non-resealable after opening;

an antiseptic wipe infused with an antiseptic material, the antiseptic wipe being positioned within the interior compartment of the bacteria-proof packaging container without additional antiseptic wipes, and wherein the antiseptic wipe has a rolled cylindrical shape formed as a tight spiral with multiple overlapping layers;

a first portion of the bacteria-proof packaging container tearable from a second portion of the bacteria-proof packaging container, wherein the first portion is separatable from the second portion to expose one cylindrical end of the antiseptic wipe in the rolled cylindrical shape while another cylindrical end of the antiseptic wipe in the rolled cylindrical shape remains within the bacteria-proof packaging container, wherein the medical professional only touches the bacteria-proof packaging container when contacting the exposed cylindrical end of the antiseptic wipe in the rolled cylindrical shape to the patient's skin and wherein the rolled cylindrical shape of the antiseptic wipe has an axial rigidity that substantially exceeds the rigidity of fabric material of the antiseptic wipe in a flat sheet form to resist axial deflection of the antiseptic wipe when the exposed cylindrical end of the antiseptic wipe is contacted against the patient's skin and a lateral force is applied to the exposed cylindrical end of the antiseptic wipe; and at least a first tab and a second tab formed on the bacteria-proof packaging container, wherein separation of the first tab from the second tab causes the first portion to separate from the second portion.

10. The single-use, disposable antiseptic wipe apparatus of claim 9, wherein the bacteria-proof packaging container further comprises a horizontal tear structure positioned substantially proximate to the first portion of the bacteria-proof packaging container.

11. The single-use, disposable antiseptic wipe apparatus of claim 9, wherein the bacteria-proof packaging container further comprises a vertical tear structure positioned between the first portion and the second portion, and axially along the bacteria-proof packaging container.

12. The single-use, disposable antiseptic wipe apparatus of claim 6, wherein the bacteria-proof packaging container further comprises a vertical tear structure positioned between the first portion and the second portion, and axially along the bacteria-proof packaging container, wherein the vertical tear structure is connected to the first tab pullable by the medical professional to open the bacteria-proof packaging container along an elongate axis, and wherein the first portion of the bacteria-proof packaging container separates from the second portion of the bacteria-proof packaging container along an adhesive edge.

13. The single-use, disposable antiseptic wipe apparatus of claim 9, wherein the bacteria-proof packaging container further comprises a plurality of perforations along two opposite sides of the bacteria-proof packaging container, and wherein the single-use, disposable antiseptic wipe apparatus is guidable along a belt by the plurality of perforations.

14. The single-use, disposable antiseptic wipe apparatus of claim 9, wherein the first portion of the bacteria-proof packaging container is smaller than the second portion of the bacteria-proof packaging container in which the antiseptic wipe in the rolled cylindrical shape remains.

15. The single-use, disposable antiseptic wipe apparatus of claim 9, wherein the antiseptic wipe in the rolled cylindrical shape is not folded.

16. The single-use, disposable antiseptic wipe apparatus of claim 9, wherein the antiseptic wipe in the rolled cylindrical shape is also folded.

* * * * *